United States Patent [19]

Ivy et al.

[11] Patent Number: 4,933,364
[45] Date of Patent: *Jun. 12, 1990

[54] PROCESS FOR PROMOTING GROWTH AND FEED EFFICIENCY OF FOOD PRODUCING MAMMALS

[75] Inventors: Richard E. Ivy; David R. Bright; Robert D. Williams, all of Terre Haute, Ind.

[73] Assignee: International Minerals & Chemical Corp., Terre Haute, Ind.

[*] Notice: The portion of the term of this patent subsequent to Aug. 2, 2005 has been disclaimed.

[21] Appl. No.: 149,950

[22] Filed: Jan. 29, 1988

Related U.S. Application Data

[63] Continuation of Ser. No. 852,078, Apr. 14, 1986, abandoned, which is a continuation of Ser. No. 512,319, Jul. 11, 1983, abandoned, which is a continuation of Ser. No. 139,560, Apr. 11, 1980, abandoned, which is a continuation of Ser. No. 56,644, Jul. 11, 1979, abandoned.

[51] Int. Cl.$^5$ .............................................. A61K 31/35
[52] U.S. Cl. ..................................................... 514/460
[58] Field of Search ........................................ 514/460

[56] References Cited

U.S. PATENT DOCUMENTS

| | | | |
|---|---|---|---|
| 3,705,238 | 9/1970 | Hamill et al. | 424/121 |
| 3,794,732 | 2/1974 | Raun | 424/283 |
| 3,839,557 | 10/1974 | Raun | 424/115 |
| 3,923,823 | 12/1975 | Gale et al. | 424/272 X |
| 3,937,836 | 2/1976 | Raun | 424/283 |
| 4,033,823 | 7/1977 | Liu et al. | 195/80 |
| 4,129,578 | 12/1978 | Celmer et al. | 424/283 X |
| 4,148,890 | 4/1979 | Czok et al. | 424/181 |
| 4,161,520 | 7/1979 | Osborne et al. | 424/115 |
| 4,192,887 | 3/1980 | Cloyd et al. | 424/283 |
| 4,218,443 | 8/1980 | Comai et al. | 424/181 |
| 4,305,956 | 12/1981 | Shibuya et al. | 424/283 |
| 4,761,426 | 8/1988 | Martin et al. | 514/460 |

OTHER PUBLICATIONS

*Biochemistry*, vol. 15, No. 5 (1976) 935–43.
Westley, *Advances in Applied Microbiology*, 22, 177–223 (1977).
Mitani et al., *the Journal of Antibiotics*, "Studies on the Ionophorous Antibiotics", vol. XXX, No. 3, pp. 239–243.
Hammond et al., *Journal of Animal Science*, vol. 51, No. 1, "Inhibition of Ruminal Degradation of L–Tryptophan to 3–Methylindole, Invitro".
Otake et al., *Agric. Biol. Chem.*, "The Assignment of the C–NMR Spectrum of Lysocellin and its Biosynthesis".
Ebata et al., *the Journal of Antibiotics*, vol. XXVIII, pp. 118–121 (Feb. 1975).
Otake et al., *J.C.S. Chem. Comm.*, pp. 92–93 (1975).

*Primary Examiner*—Frederick E. Waddell
*Attorney, Agent, or Firm*—Bernard, Rothwell & Brown

[57] ABSTRACT

A process for promoting growth and feed efficiency in food producing mammals is provided by administering to such mammals, growth promoting amounts of a zinc complex of a polyether antibiotic selected from the group consisting of monensin, nigericin, salinomycin, narasin, noborotomycin A and B, SY-1, grisorixin, X-206, lonomycin, laidlomycin, mutalomycin, alborixin, lasalocid and lysocellin.

Zinc complexes of this type are prepared by adding soluble zinc salt to a fermentation beer containing a polyether antibiotic to thereby form an insoluble, recoverable biomass containing the desired growth-promoting zinc complex for use in the process herein.

11 Claims, No Drawings

PROCESS FOR PROMOTING GROWTH AND FEED EFFICIENCY OF FOOD PRODUCING MAMMALS

This application is a continuation of U.S. Ser. No. 06/852,078, filed Apr. 14, 1986, now abandoned, which is a continuation of U.S. Ser. No. 06/512,319, filed July 11, 1983, now abandoned, which is a continuation of U.S. Ser. No. 06/139,560, filed Apr. 11, 1980, now abandoned, which is a continuation-in-part of U.S. Ser. No. 06/056,644, filed July 11, 1979, now abandoned.

The present invention relates to animal growth-promoting processes which utilize zinc complexes of polyether antibiotics as growth-promoting substances in food-producing mammals, particularly to those which use zinc complexes of linear monovalent polyether antibiotics and non-nitrogen containing divalent polyether antibiotics.

Polyether antibiotics can be generally characterized as carboxylic acid ionophores which can be produced by culturing Streptomyces type microorganisms. These polyether antibiotics have a basic structure consisting essentially of the elements oxygen, hydrogen and carbon and possibly nitrogen and have a molecular weight in the range of about 300 to about 1800, most often from about 400 to about 1200. They have low solubility in water, are generally soluble in low molecular weight alcohols, ethers and ketones, and have at least one, and usually one or two, carboxylic acid groups. A fairly comprehensive review of this class of antibiotics is set forth in Westley, *Adv. Appl. Microbiology* 22, 177–223 (1977). As is mentioned therein, at least twenty different polyether antibiotics were known at the time the article was written. Since then, additional polyether antibiotics have been discovered.

In the previously noted publication, Westley classified the known polyether antibiotics into four separate classes based on ability of the particular antibiotic to effect the transport of divalent cations and based on the chemical structure of the particular antibiotic. Using these criteria, Westley defined class 1a as those polyether antibiotics which are monovalent polyether antibiotics. In addition, the polyether antibiotics of this class have a generally linear configuration, i.e., the carboxylic portion of the polyether molecule is attached either directly or indirectly to a terminal ring structure. They generally include from about four to about six tetrahydropyran and/or -furan structures and up to six total ring structures. Included in class 1a are the polyether antibiotics monensin, laidlomycin, nigericin, grisorixin, SY-1, salinomycin, narasin, lonomycin, X-206, noboritomycins A and B, mutalomycin, and alborixin. For the purpose of clarity, the polyether antibiotics of this class are hereinafter referred to as "linear monovalent polyether antibiotics."

Class 1b of the polyether antibiotics was defined by Westley as monovalent monoglycoside polyether antibiotics. These polyether antibiotics, as the class name suggests, include a glycoside type structure, more specifically, a 2,3,6-trideoxy-4-O-methyl-D-erythrohexapyranose moiety, which is attached to the polyether molecule such that a non-linear type molecule is formed, i.e., the carboxylic portion of the polyether molecule is attached either directly or indirectly to a non-terminal ring structure or the molecule has a side chain ring structure, e.g., a 2,3,6-trideoxy-4-O-methyl-D-erythrohexapyranose moiety. Generally, the polyether antibiotics of this class contain about six or seven tetrahydropyran and/or -furan structures.

Class 2a as defined by Westley is divalent polyether antibiotics. These antibiotics are generally of a linear configuration and may contain from about two or about three tetrahydropyran and/or -furan structures, up to three total ring structures and no nitrogen atoms. Included within class 2a are the antibiotics lasalocid and lysocellin. For the purpose of clarity, the polyether antibiotics of this class are hereinafter referred to as "non-nitrogen containing divalent polyether antibiotics." Class 2b of the polyether antibiotics is divalent pyrrole ethers and thus, in contrast to the antibiotics of the other classes, these antibiotics contain one or more nitrogen atoms.

As was mentioned above, one of the polyether antibiotics in class 2a as defined by Westley is the lasalocid polyether antibiotic. Lasalocid was discovered by Julius Berger et al. in media fermented with a Streptomyces microorganism isolated from a sample of soil collected at Hyde Park, Mass. [Cf. Berger et al., *J. Amer. Chem. Soc.* 73, 5295–8 (1951)]. Originally this material was known by the code name X-537A, and the generic name "lasalocid" was subsequently assigned to the material. Sometime in the late 1960s, it was found that lasalocid was a coccidiostat active against such organisms as *Eimeria tenella, Eimeria necatrix, Eimeria acervulina, Eimeria brunetti, Eimeria mivati* and *Eimeria maxima* (Stempel et al., U.S. Pat. No. 3,715,372, issued Feb. 6, 1973). On Oct. 8, 1976, the Food and Drug Administration granted approval for the sale of the sodium salt of lasalocid as a coccidiostat for chickens. Monensin and nigericin are also polyether antibiotics having coccidiostatic properties. [Cf. *Merck Index*, 9th Ed. (1976) No. 6081 (monensin); Steinrauf et al., *Biochem. and Biophs. Res. Comm.* 33, 29–31 (1968); Stempel et al. *J. Antibiotics* 22, 384–5 (1969); and Harned et al. Antibiot. and Chemotherapy 1, 594–6 (1951)]. Other polyether antibiotics for which a coccidiostatic activity has been alleged include salinomycin and narasin.

Many of the polyether antibiotics have generally heretofore been recovered and employed as the form of their sodium salts. Further, novel zinc complexes of these antibiotics can be prepared and employed as coccidiostats and growth-promoting agents for poultry in accordance with the procedures set forth in the concurrently filed, copending U.S. patent application of Jerome L. Martin, said application having Ser. No. 139,567.

While the antibiotic and coccidiostatic efficacy of many polyether antibiotics has heretofore been recognized, it has now been surprisingly discovered that the zinc complexes of polyether antibiotics also act as especially effective growth-promoting and feed efficiency-enhancing agents when administered to food-producing mammals such as ruminants. Without being bound by any particular theory, it appears that the mechanism by which such zinc complexes promote growth in food-producing mammals is significantly different from that which is involved when these same zinc materials are administered to poultry. For example, in ruminants having a developed rumen function, including cattle, sheep and goats, the zinc complexes herein are believed to promote growth and enhance the efficiency of feed utilization in the animal by lowering the acetate/propionate ratio within the volatile fatty acids (VFA) found in the animal's rumen fluid. The relationship between acetate/propionate ratio in the rumen and feed efficiency in the ruminant animals is explained in greater detail in Raun; U.S. Pat. No. 3,794,732, issued Feb. 26, 1974.

Therefore, in one aspect, the present invention relates to processes for promoting growth and enhancing feeding efficiency in food-producing mammals by administering zinc complexes of polyether antibiotics. Polyether antibiotics useful as zinc complexes in the growth promoting processes of the present invention include linear monovalent polyether antibiotics and non-nitrogen containing divalent polyether antibiotics, i.e., those polyether antibiotics falling within classes 1a and 2a as defined by Westley. These classes of polyether antibiotics include the antibiotics monensin, nigericin, salinomycin, narasin, noboritomycin A and B, grisorixin, X-206, laidlomycin, lonomycin, SY-1, mutalomycin, alborixin, lasalocid and lysocellin. Preferred polyether antibiotics useful as zinc complexes in the growth promoting processes of the present invention include monensin, lasalocid and lysocellin. For convenience, the term "zinc complex" or "complex" will be used hereinafter as meaning "a zinc complex of polyether antibiotic."

In accordance with the present invention, zinc complexes of the polyether antibiotics can be formed by adding water-soluble zinc salts to the fermentation broth in which such antibiotics have been prepared, and the resulting broth-insoluble zinc complexes of the antibiotics can then be recovered from the broth and employed as growth-promoting and feed efficiency enhancing additives, especially in feed for food-producing mammals such as ruminants and swine.

Antibiotic-containing fermentation broth can be prepared in conventional manner by fermenting a nutrient-containing liquid fermentation medium inoculated with a Streptomyces microorganism capable of producing the desired antibiotic. Suitable liquid fermentation media are generally aqueous dispersions containing a nitrogen source and a carbohydrate source. Nitrogen sources for use in the fermentation media herein can include, for example, yeast, yeast-derived products, corn meal, bean meal, e.g., soy bean meal, etc. Carbohydrate sources for use in the fermentation media herein can include, for example, sugar, molasses, corn-steep liquor and the like. The fermentation media can also contain a variety of optional ingredients, if desired, such as for example, pH adjustment agents, buffers, trace minerals, antifoam agents, filter aids, etc.

The antibiotic can be prepared by growing the Streptomyces microorganism in an aerated, agitated, submerged culture with the pH of the broth adjusted to about neutral, i.e., from about 6.5 to about 7.5. Fermentation can generally be carried out at slightly elevated temperatures, e.g., between about 25° C. and 35° C. Incubation of the broth can be carried out for a period of several days, e.g., from about 4 to 6 days or longer if it is economically advantageous to do so.

As was mentioned previously, polyether antibiotics for forming zinc complexes for use in the processes in accordance with the present invention include linear monovalent polyether antibiotics and non-nitrogen containing divalent polyether antibiotics, i.e., those polyether antibiotics which fall within classes 1a and 2a as defined by Westley, and which include monensin, nigericin, salinomycin, SY-1, narasin, laidlomycin, noboritomycin A and B, grisorixin, X-206, mutalomycin, alborixin and lonomycin; and lasalocid and lysocellin; respectively.

Monensin can be produced by inoculating the fermentation medium with a Streptomyces cinnamonensis microorganism. Such a microorganism is on unrestricted deposit under the number ATCC 15413 at the American Type Culture Collection, 12301 Parklawn Drive, Rockville, Md. 20852 (hereinafter referred to as the American Type Culture Collection).

Monensin is characterized chemically as 2-[5-ethyltetrahydro-5-[tetrahydro-3-methyl-5-[tetrahydro-6-hydroxy-6-(hydroxymethyl)-3,5-dimethyl-2H-pyran-2-yl]-2-furyl]-2-furyl]-9-hydroxy-β-methoxy-α,γ,2,8-tetramethyl-1,6-dioxaspiro[4.5]decane-7-butyric acid. This material has the following structural formula:

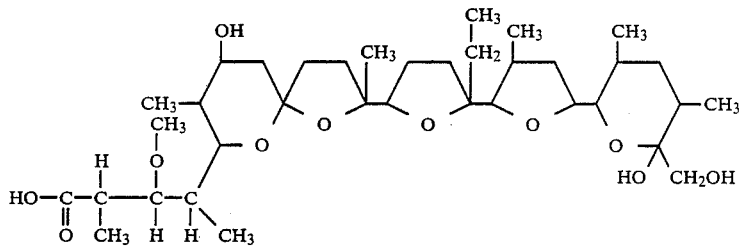

Monensin

Monensin is described in greater detail in U.S. Pat. Nos. 3,501,568 and 3,794,732.

Nigericin can be produced by inoculating the fermentation medium with a Streptomyces violaceoniger microorganism. Such a microorganism is on unrestricted deposit at NRRL B1356 at the Northern Research and Development Division, Agricultural Research Service, U.S. Department of Agriculture, Peoria, Ill. (hereinafter referred to as the Agricultural Research Service).

Nigericin is characterized chemically as a stereoisomer of tetrahydro-6-([9-methoxy-2,4,10-trimethyl-2-[tetrahydro-5-methyl-5-[tetrahydro-3-methyl-5-tetrahydro-6-hydroxy-6-(hydroxymethyl)-3,5-dimethyl-2H-pyran-2-yl]-2-furanyl]-2-furanyl]-1,6-dioxaspiro(4.5) dec-7-yl]-methyl]-α,3-dimethyl-2H-pyran-2-acetic acid). This material has the following structural formula:

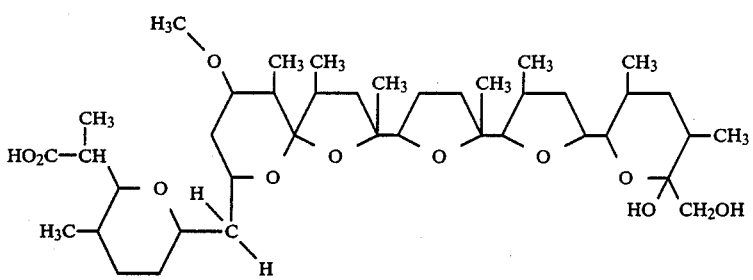

Nigericin

Nigericin is also known by the names polyetherin A, antibiotic X-464, antibiotic K178, helexin C and azolomycin M. Nigericin (and its characteristics and preparation) is described in greater detail in U.S. Pat. No. 3,555,150; U.S. Pat. No. 3,794,732, Harned et al. *Antibiotics and Chemotherapy*, Vol. 1, No. 9 (December, 1951) pp. 594–596; Steinrauf et al., *Biochemical and Biophysical Research Communications*, Vol. 33, No. 1 (1968) pp. 29–31 and Stempel et al., *The Journal of Antibiotics*, Vol. XXII, No. 8 (August, 1969) pp. 384–385.

The salinomycin antibiotic can be produced by inoculating a fermentation medium with a *Streptomyces albus* microorganism which is on deposit under number ATCC 21838 at the American Type Culture Collection mentioned previously. Salinomycin was reported by Miyazaki et al., *J. Antibiotics* 27, 814–21 (1974) as having the following structural formula:

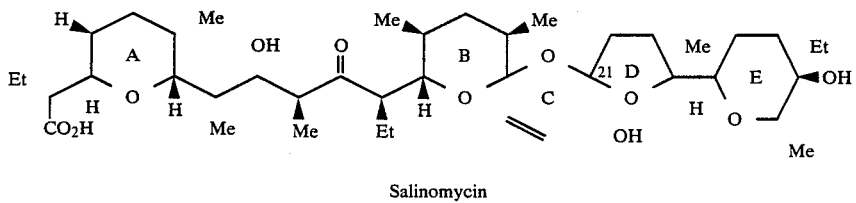

Salinomycin

This article sets forth methods of preparation and properties of salinomycin and U.S. Pat. No. 3,857,948 to Tanaka et al. also discloses methods for the preparation of the salinomycin antibiotic.

The antibiotic narasin (also known as 4-methylsalinomycin) can be produced by innoculating a fermentation medium with a *Streptomyces aureofaciens* microorganism which is on unrestricted deposit at the Agricultural Research Service mentioned previously under culture numbers NRRL 5758 and 8092. The structure of narasin was reported by Berg et al., *J. Antibiotics* 31, 1–6 (1978) as the following:

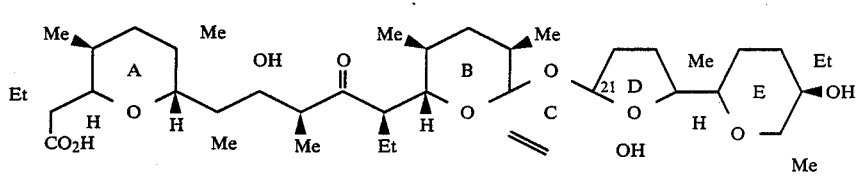

Narasin

The antibiotic is also the subject of U.S. Pat. Nos. 4,035,481 and 4,038,384 to Berg et al. The antibiotics noboritomycin A and B are the fermentation products of the microorganism *Streptomyces norboritoensis* which is on deposit at Agricultural Research Service under the number NRRL 8123. A method for the preparation of these antibiotics and their chemical structure was reported by Keller-Juslen et al. in *J. Antibiotics* 31, 820–828 (1978). The antibiotics have the structural formula:

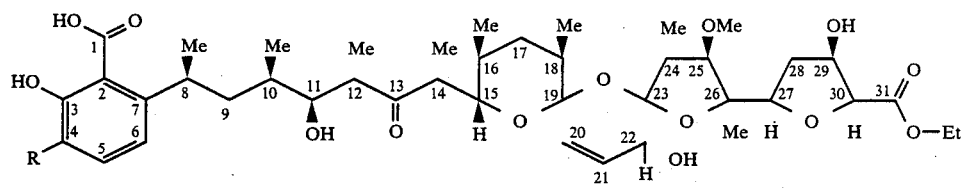

Noboritomycin A & B

In noboritomycin A, R is methyl and in norboritomycin B, R is ethyl.

The antibiotic grisorixin is produced from the microorganism *Streptomyces griseus* as reported by Gachon et al., *Chem. Comm.*, 1421–1423 (1970) and *J. Antibiotics* 28, 345–350 (1975). As is disclosed in U.S. Pat. No.

4,161,520 to Osborne et al., the microorganism is on deposit at the Institut National de la Recherche Agronomique where it has been assigned the designation INRA SAB 2142. Grisorixin is structurally very similar to nigericin, the only difference being the presence of an additional oxygen in nigericin. The structural formula for grisorixin is:

29, 354–365 (1976) as DE-3936 and was determined to be identical to emercid reported by Riche et al., *J.C.S. Chem. Comm.* 1975, 951–952 (1975) and to 31,559RP reported by Rhone Poulenc: Japan Patent, Kokai 50-129, 796 (Oct. 14, 1975). U.S. Pat. No. 3,950,514 to Sawada et al. discloses the Ionomycin antibiotic as being produced by the *Streptomyces ribosidicus* microorganism

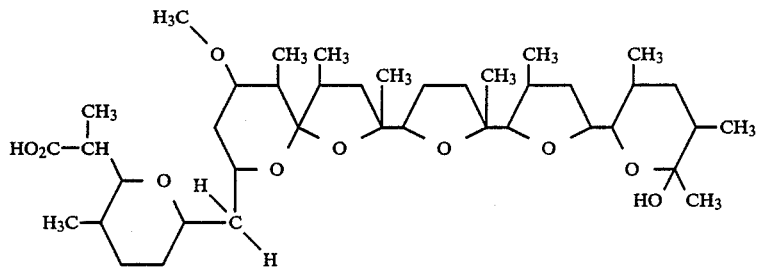

Grisorixin

Various derivatives of grisorixin are disclosed by Gachon et al., *J. Antibiotics* 28, 351–357 (1975).

Antibiotic X-206 was first reported by Berger et al., *J. Am. Chem. Soc.* 73, 5295–5298 (1951) and has the following structure as reported by Blount et al., *Chemical Communications*, 927–928 (1971):

which has been deposited under number ATCC 31051 at the American Type Culture Collection.

The following structural formula was set forth by Gachon et al., *J. Antibiotics* 29, 603–610 (1976) for the antibiotic alborixin:

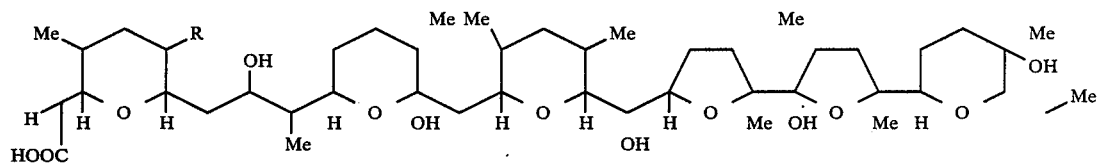

R = Me or H

Alborixin

Certain characteristics of the antibiotic were set forth in

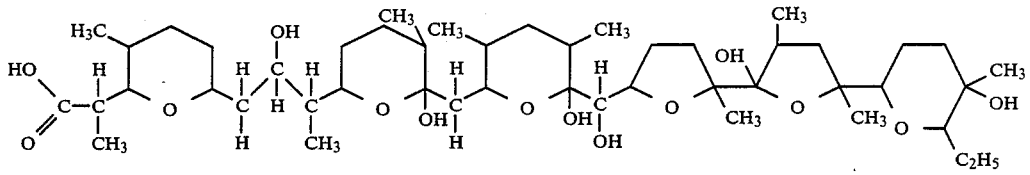

X-206

Methods for preparation of the X-206 antibiotic as well as further particulars as to its properties are set forth in U.S. Pat. Nos. 3,839,557 to Raun and 3,794,732 to Raun.

The antibiotic lonomycin has the following structural formula as reported by Mitani et al., *J. Antibiotics* 31, 750–755 (1978):

the article by Delhomme at al., *J. Antibiotics* 29, 692–695 (1976). The alborixin antibiotic is produced from a *Streptomycus albus* microorganism and as is disclosed in U.S. Pat. No. 4,161,520 to Osborne et al., the microorganism is on deposit at the Institut National de la Recherche Agronomique and assigned the designation

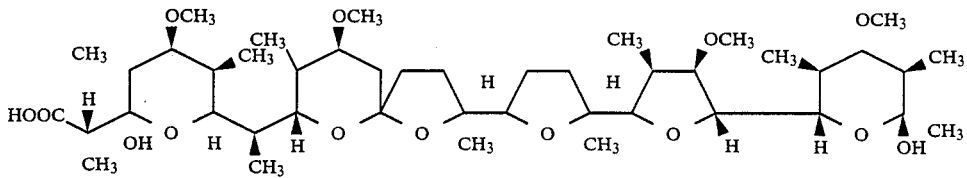

Lonomycin

A method for producing the antibiotic is set forth by Omura et al., *J. Antibiotics* 29, 15–20 (1976). The antibiotic was also identified by Oshima et al., *J. Antibiotics*

INRA SAB 3840.

Mutalomycin is produced by strain S11743/A of the *Streptomyces mutabilis* microorganism which has been deposited at the Agricultural Research Service under number NRRL 8088. A method for preparing the antibiotic and its physical and chemical properties were reported by Fehr et al. *J. Antibiotics* 30, 903–907 (1977). The structural formula of mutalomycin is:

forth in U.S. Pat. No. 4,138,496 to Shibata et al., the SY-1 antibiotic has the following structural formula:

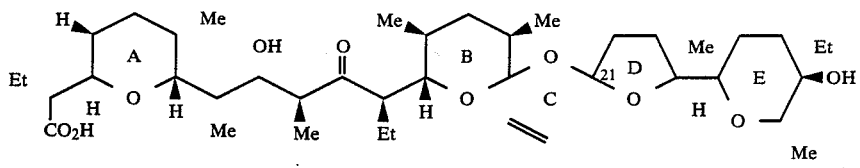

SY-1

The structure of the SY-1 antibiotic is quite similar to that of salinomycin, the only apparent structural difference being that salinomycin contains a hydroxyl group on the ring designated "C".

Lasalocid can be prepared by inoculating the fermen-

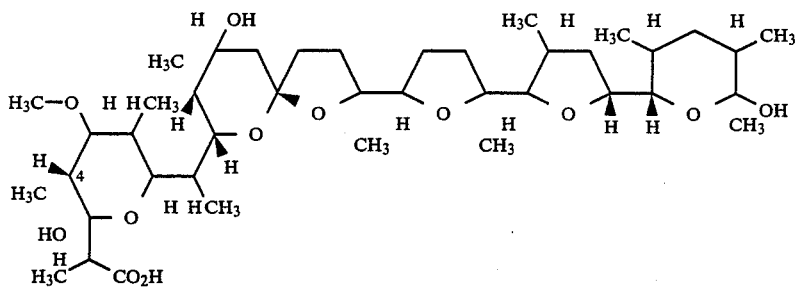

Mutalomycin as reported by Fehr et al. *J. Antibiotics* 32, 535–536 (1979).

The antibiotic laidlomycin has been described by Kitame et al., *J. Antibiotics* 27, 884–887 (1974), the antibiotic being produced by the *Streptomyces eurocidicus* var. *asterocidicus* microorganism which has been indexed as species S-822 at the Department of Bacteriology, Tohoku University School of Medicine, Sendai, Japan. The chemical structure of laidlomycin was reported by Westley, *Adv. Appl. Microbiology* 22, 177–223 (1977) as being:

tation medium with a *Streptomyces lasaliensis* microorganism. Lyophilized tubes of this culture bearing the laboratory designation X-537A were deposited with the U.S. Department of Agriculture, Agricultural Research Service, North Utilization Research and Development Division, Peoria, Ill. The culture, given identification number NRRL 3382R by the Agricultural Research Service, has been made available to the public through NRRL.

The lasalocid antibiotic produced has been chemically identified in U.S. Pat. No. 4,164,586 to Westley as

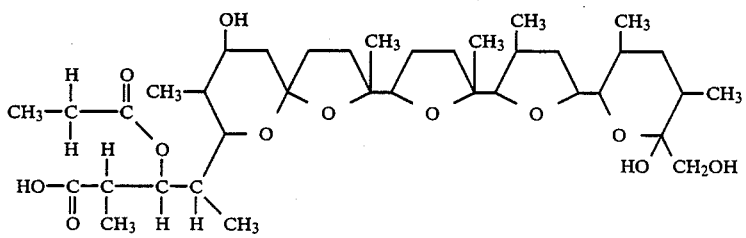

Laidlomycin

The laidlomycin antibiotic also appears to be the subject of U.S. Pat. No. 4,016,256 to Ishida et al.

The antibiotic SY-1 is the fermentation product of a *Streptomyces albus* microorganism, a culture of which has been deposited at the American Type Culture Collection under accession number ATCC 21838. As is set 6-{7(R)-[5(S)-ethyl-5(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5-(S)-dimethyl-6-oxononyl}-2,3-cresotic acid. This antibiotic has the following structural formula:

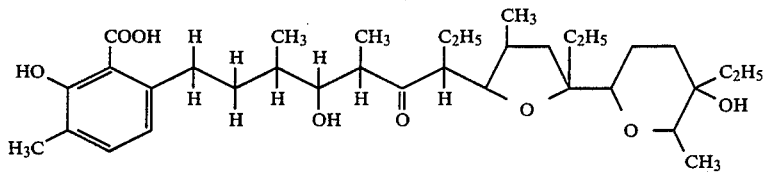

Lasalocid

A method for producing the antibiotic lysocellin was disclosed by Liu et al. in U.S. Pat. No. 4,033,823 by the cultivation of a strain of *Streptomyces longwoodensis* which is on deposit at the American Type Culture Collection under the designation ATCC 29251. The structure of lysocellin is as follows:

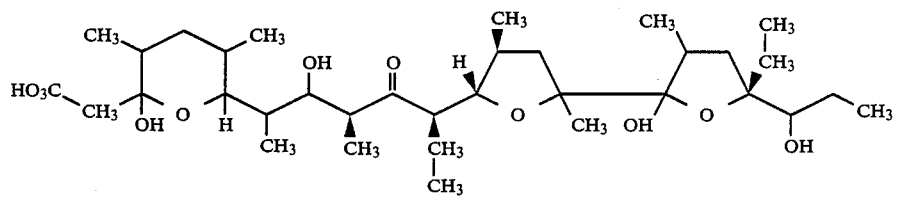

Lysocellin

Suitable methods for preparing the lysocellin antibiotic are set forth in the above-mentioned patent. The characteristics of lysocellin were first set forth in the article by Ebata et al., *J. Antibiotics* 28, 118–121 (1975).

While the above descriptions of the various known polyether antibiotics have generally identified the antibiotics as being single compounds, it should be recognized that at least some of the polyether antibiotics are produced as an antibiotic complex of structurally related factors containing varying proportions of each factor. As an example, the structure for lasalocid set forth previously is lasalocid factor A which is produced in combination with factors B-E in ratios depending upon fermentation conditions. Homologs of lasalocid A are disclosed in U.S. Pat. No. 4,168,272 to Westley. An isomeric form of lasalocid is also known from U.S. Pat. No. 3,944,573 to Westley. In addition, monensin is produced with factors B and C as reported by Westley, *Adv. Appl. Microbiology* 22, 200 (1977) and narasin is produced with factors A, B and D as is set forth in U.S. Pat. No. 4,038,384 to Berg et al. It should therefore be realized that the present invention comprehends the use of the zinc complexes of the various factors of the polyether antibiotics whether in combination with other factors or in their isolated form in promoting growth and enhancing feeding efficiency in food producing mammals.

Furthermore, zinc complexes of derivatives of the previously mentioned polyether antibiotics are also within the scope of the present invention. For example, various derivatives of the lasalocid antibiotic are known from U.S. Pat. No. 3,715,372 to Stempel et al. In addition, derivatives of monensin are disclosed in U.S. Pat. No. 3,932,619 to Brannon et al. which is directed to a metabolite produced from monensin, U.S. Pat. No. 3,832,258 to Chamberlain which is directed to the deshydroxymethyl derivative of monensin and U.S. Pat. Nos. 4,141,907 and 4,174,404 to Nakatsukasa et al. are directed to deoxynarasin. Therefore, as used herein, the specific name of the polyether antibiotic, e.g. lasalocid, encompasses all of the factors of the antibiotic, e.g. lasalocid A-E, as well as isomers thereof, e.g. iso-lasalocid, and derivatives thereof.

For further particulars as to characteristics and methods for the preparation of certain of the above polyether antibiotics, reference is made to U.S. Pat. No. 3,995,027 to Gale et al. and the patents cited therein and to U.S. Pat. No. 3,794,732 to Raun and the patents and articles cited therein.

To the extent necessary, the above-mentioned patents and literature articles mentioned in describing the various known polyether antibiotics are incorporated herein by reference.

To prepare the polyether antibiotics employed in the processes of the present invention, the antibiotic, generally in the form of its alkali metal, alkaline earth metal or ammonium salt, is treated in situ in the fermentation broth or beer by adding to the antibiotic containing broth a water-soluble zinc salt. Addition of such a water-soluble zinc salt promotes the formation of a zinc complex of the polyether antibiotic. Such a zinc complex of the antibiotic, along with zinc complexes formed with residual nitrogen-containing compounds in the broth such as amino acids, polypeptides, and proteins, are insoluble in the fermentation broth liquid.

The zinc ions from the added zinc salt apparently form coordination bonds with the oxygen atoms of the insoluble zinc antibiotic complex. For example, the structure of the zinc complex of lasalocid is believed to be represented by the following:

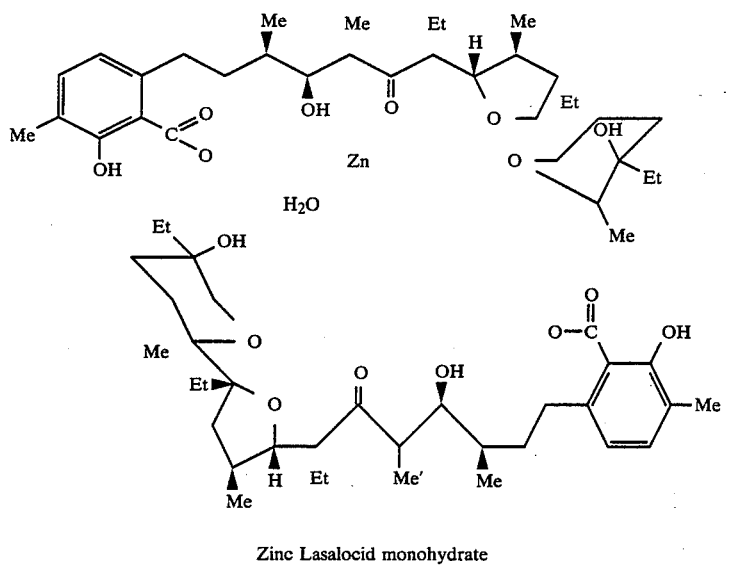

Zinc Lasalocid monohydrate

On the basis of the formation constants with ligands such as citric acid, lactic acid, and tartaric acid, zinc ions form stronger bonds with oxygen-containing compounds than do ions such as $Mg^{++}$, $Ca^{++}$, $Ba^{++}$, $Na^+$, and $K^+$.

The zinc salt added to the fermentation broth can be various water-soluble salts which ionize in the fermentation broth. Such salts include, for example, zinc chloride, zinc sulfate, zinc acetate, zinc benzoate, zinc citrate, zinc lactate, etc. Water-soluble zinc salts are generally those which can be dissolved to the extent of about 1 percent by weight or more in water at 20° C. For maximum production of the desired zinc complexes, water-soluble zinc salt should be added to the fermented broth in an amount which is sufficient to fill substantially all of the possible zinc coordination sites of the proteins, polypeptides, amino acids and related compounds, in addition to substantially all of the available coordination sites of the antibiotic present. This is necessary because in general, nitrogen atoms in the polypeptides, amino acids, etc., form stronger coordination bonds with zinc than do the oxygen atoms in the polyether antibiotic. Generally, therefore, zinc salt is added to the fermentation broth in an amount sufficient to provide a zinc content of from about 3 to 12 percent and preferably from about 5 to 10 percent by weight of the dried precipitate recovered from the fermentation broth as hereinafter more fully described.

The amount of soluble zinc salt to be added will depend on the amount of nutrients added to the fermentation broth during the course of the fermentation. An actual amount of soluble zinc salt to be added to broth obtained from a given mash bill can be determined by simple laboratory precipitations followed by zinc analyses on the dried precipitates. When, for example, the preferred zinc chloride salt is employed to form the desired zinc antibiotic complex, advantageously from about 4 to 10 gallons of a 67 weight percent zinc chloride solution (sp. gr. 1.883), can be added to 1000 gallons of fermentation broth.

To form the zinc antibiotic complex in the fermentation broth, pH of the broth is advantageously adjusted to about 6.5 to 7.5 and preferably to about 6.8 to 7.2 after addition of the soluble zinc salt to the fermentation broth.

The insoluble zinc complexes formed upon addition of zinc salt can be readily separated from the fermentation broth or beer by conventional filtration or centrifugation techniques. In this manner, a wet biomass, containing the zinc antibiotic complex, is realized. This wet biomass is resistant to wild fermentations because of its relatively high zinc content. The wet biomass so obtained is easily dried by spray drying or drum drying procedures, and this zinc antibiotic-containing dried product can then be used as a feed additive per se. If the antibiotic content of the fermentation beer is lower than desired after completion of the fermentation, crude antibiotic in its sodium salt form can be added to the fermentation beer prior to the addition of the soluble zinc salt. In this manner, the antibiotic content of the biomass composition to be separated from the broth can be increased. To be suitable as a feed additive, the dried biomass preferably contains at least about 5 percent by weight of the zinc antibiotic complex, advantageously from about 10 percent to 50 percent by weight of the zinc antibiotic complex.

Recovery of the zinc antibiotic complexes in the manner described herein provides several important advantages over known antibiotic preparation and recovery processes. The procedure described herein, for example, provides a means for recovering relatively high yields of antibiotic in a salable feed additive product. Further, the use of expensive extraction solvents and the cost associated with the process losses of such solvents are avoided. The procedure described herein also permits recovery of salable feed values present in the mycelium of the Streptomyces microorganism used to produce the antibiotic. The recovery procedure described herein further reduces the cost of waste disposal operations needed in previous processes to deal with the mycelial mat produced during fermentation. Use of this mat as part of the feed additive product, in fact, reduces the cost of the carrier for the antibiotic material being marketed.

The zinc antibiotic complexes used in the present invention act as growth-promoting agents in food-producing mammals, e.g., ruminants and swine. Such zinc complexes can be administered to food-producing mammals, either orally or parenterally, in amounts sufficient to enhance the growth rate of the animal. Ruminants are the preferred hosts for enhanced growth. The amount of zinc complex administered to an animal varies, of course, with the animal, the desired rate of growth, and the like. The zinc complex is frequently administered to ruminants in an amount of about 1 to 200, preferably about 1 to 50 milligrams per head per day.

Preferably, the zinc antibiotic complexes herein are administered to food-producing mammals in their feed. As noted, the zinc antibiotics complex can be conveniently added to animal feed in the form of the dried, antibiotic-containing biomass which is recovered as a feed additive composition from the fermentation broth as hereinbefore described. When the zinc growth-promoting complexes herein are to be administered to food-producing mammals in their feed, a feed composition may be prepared containing the usual nutritionally-balanced quantities of carbohydrates, proteins, vitamins, and minerals as diluents together with the zinc antibiotic complex. Some of the usual sources of these dietary elements are grains, such as ground grain and grain by-products; animal protein substances, such as those found in fish meal and meat scraps; vegetable proteins, such as soybean oil meal or peanut oil meal; vitaminaceous materials, e.g., mixture of vitamins A and D, riboflavin supplements and other vitamin B complex members; and bone meal and limestone to provide minerals. A type of conventional feed material for use with cattle, for example, includes alfalfa hay and ground corn cobs, together with supplementary vitaminaceous substances if desired. The zinc complexes of the present invention can generally be employed in the feed compositions to the extent of from about 15 grams per ton to 200 grams per ton, preferably from about 75 grams per ton to 125 grams per ton.

The zinc complex growth-promoting agents herein, can also be administered to food-producing mammals parenterally in combination with a pharmaceutically-acceptable carrier. For example, the zinc antibiotic complex can be employed in an injection composition or as an implant under the skin. Advantageously, the compounds can be suspended in a suitable injection suspension medium, such as peanut oil, and injected parenterally. Administration of the growth-promoting agents herein in this manner can include intramuscular, intravenous, and intraperitoneal injections. When an implant is used, for example a ball or cylindrical implant inserted under the skin on the ear of an animal, the implant will generally contain from about 1 mg. to 100 mg. of the zinc complex.

The zinc complexes, the complex preparation and recovery processes and the feed and feed additive compositions involved in the present invention as well as the usefulness of the zinc complexes herein as growth-promoting agents for ruminants are illustrated by the following examples. Such examples include the preparation, recovery and evaluation of the preferred zinc lasalocid material but are in no way limiting of the present invention to processes involving that particular material.

EXAMPLE I

A. Fermentation

About 450 ml of inoculum of *Streptomyces lasaliensis* culture No. NRRL 3382R, obtained from the Ukrthern Utilization Laboratory, Peoria, Ill., is introduced into 9,000 ml of fermentation medium of the following composition:

| | |
|---|---|
| Soybean Flour | 2% |
| Brown Sugar | 2% |
| Corn Steep Liquor | 0.5% |
| $K_2HPO_4$ | 0.1% |
| Hodag Antifoam K-67 | 0.05% |
| Water | Balance |
| | 100.00% |

The fermentation is conducted in a 20-liter, stainless steel fermentor using the conditions listed below.
1. Amount of medium—9.45 liters.
2. Temperature—28° C.
3. Air Flow—9.0 liters per minute.
4. Mechanical agitation—One 13-cm. diameter impeller rotating at 600 RPM.
5. Back pressure—about 16.7 psig.
6. Time of fermentation—72 hours.

At the end of the fermentation the lasalocid assay of the beer is 1.5 g per liter.

B. Recovery

Since the assay of the beer for lasalocid is low compared to assays commonly obtained for antibiotics, the beer is spiked with crude lasalocid which has been obtained by extracting with butyl acetate a commercial product containing approximately 81 grams of sodium lasalocid per pound.

Twenty-five grams of crude sodium lasalocid (78.5% lasalocid) dissolved in 150 ml of methanol are added to 2000 ml of beer under constant agitation. After thorough agitation, 12.5 ml of a zinc chloride solution (0.24 g Zn per ml) are slowly added with agitation to the fermented beer. The pH is adjusted to a value in the range 7.0–7.4.

After the treated beer has been agitated for about 30 minutes it is filtered, without filter aid, on a Buckner funnel using No. 1 Whatman filter paper. The filtration proceeds rapidly to give a firm cake which is dried in an oven. The final dried product weighs 57 grams and has an assay of 32.7% lasalocid.

The calculated recovery from beer to dried product is 82.4% derived from the following formula.

$$\frac{0.327 \times 57}{2 \times 1.5 + 25 \times 0.785} \times 100\% = 82.4\%$$

EXAMPLE II

Administration of zinc lasalocid growth-promoting agent to cattle via cattle feed composition is illustrated by this example. A cattle feed formulation having the following composition is prepared:

| Component | Concentration |
|---|---|
| Cracked Corn | 68.5% |
| Alfalfa Meal | 5.0% |
| Ground Cobs | 10.0% |
| Soybean meal (50% protein) | 15.0% |
| Mineral Mixture | 1.0% |
| Salt | 0.5% |
| | 100.0% |

To such a composition is added enough of the zinc lasalocid-containing dried product of Example I to provide a feed composition containing about 100 grams of zinc lasalocid per ton of feed composition.

The zinc lasalocid-containing feed composition is fed to cattle in amounts sufficient to provide from about 5 to 100 ppm of zinc lasalocid in the rumen fluid. Administration of the zinc lasalocid material in this manner serves to promote cattle growth by enhancing the efficiency with which the cattle so treated utilize their feed.

EXAMPLE III

The tendency of zinc lasalocid antibiotic to desirably affect acetate/propionate ratios in rumen fluid from cattle is demonstrated by means of an in vitro rumen fluid analysis procedure. Rumen fluid is obtained from a steer which has a surgically installed fistula opening into the rumen. The steer is maintained on a grain diet consisting of the feed composition set forth in Example II. A sample of rumen fluid is strained through four layers of cheesecloth and the eluate collected. An equal amount of buffer solution with a pH of 7 is added to the rumen fluid. Ten ml of the diluted rumen fluid is placed in flasks with 500 mg of the same feed shown above which has been finely ground. Each of materials to be tested is weighed into a separate test flask. Four control flasks are also employed. All of the test flasks are incubated for 24 hours at 39° C. At the end of incubation, a pH is measured and one drop of mercuric chloride is added to each flask. The samples are centrifuged at 3000×g for 15 minutes and the supernatant is analyzed by gas chromatographic methods for volatile fatty acids.

Analyses for acetate, propionate and butyrate compounds are performed. The results are statistically compared with the results of the analyses of the control flasks. The acetic/propionic ratios are calculated for each treatment. Treatments with propionate production significantly higher than the control are evidenced in this ratio expression by lesser numbers. These treatments are then regarded as active treatments. Results of two such tests are set forth in TABLES I and II.

TABLE I

Effect of Zinc Lasalocid on Acetate/Propionate Ratios of In Vitro Ruminal Fluid

| Item* | Control | Rumensin 5 ppm | Zinc Lasalocid, ppm | | | |
|---|---|---|---|---|---|---|
| | | | 5 | 10 | 20 | 100 |
| Acetate/propionate | 1.90 | 1.06 | 1.47 | 1.30 | 1.16 | 1.00 |

*Means of seven experiments, 3 reps/treatment

TABLE II

Effect of Zinc Lasalocid on Acetate/Propionate Ratios of In Vitro Ruminal Fluid

| Item* | Control | Rumensin 5 ppm | Zinc Lasalocid, ppm | | |
|---|---|---|---|---|---|
| | | | 20 | 100 | |
| Acetate/propionate | 1.37 | 1.09 | 0.94 | 1.02 | |

*Means of four experiments, 4 reps/treatment

The data in Tables I and II demonstrate that the presence of zinc lasalocid in the rumen fluid can beneficially increase the production of propionate within the rumen relative to acetate production. Cattle wherein such a propionate increase occurs are more efficiently able to utilize their feed in the production of meat and milk.

EXAMPLES IV-XVI

Other preferred zinc complexes of polyether antibiotics are produced and recovered and the resultant complexes are used as growth-promoting agents in food producing mammals. The polyether antibiotics utilized in the examples are monensin, nigericin, salinomycin, narasin, noboritomycin A and B, lysocellin, grisorixin, X-206, lonomycin, laidlomycin, SY-1, mutalomycin and alborixin.

Each of the zinc complexes is produced and recovered by a process similar to that set forth in Example I except that the appropriate microorganism is utilized instead of the lasalocid producing microorganism. The recovered zinc complex of each antibiotic is formulated into a feed composition similar to the composition set forth in Example II and fed to cattle in amounts sufficient to provide from about 5 to 100 ppm of the zinc complex in the rumen fluid during rumination. Positive effects are realized for each polyether antibiotic in its zinc complexed form in promoting growth and feed efficiency in cattle. The results are set forth below in tabular form, an "X" indicating that a positive effect is realized by the use of a particular zinc complex.

TABLE III

| Example Number | Polyether Antibiotic Zinc Complex | Cattle Growth Promotion | Example Number | Polyether Antibiotic Zinc Complex | Cattle Growth Promotion |
|---|---|---|---|---|---|
| IV | Noboritomycin | X | XI | Lonomycin | X |
| V | Monensin | X | XII | X-206 | X |
| VI | Laidlomycin | X | XIII | Alborixin | X |
| VII | Nigericin | X | XIV | SY-1 | X |
| VIII | Grisorixin | X | XV | Lysocellin | X |
| IX | Salinomycin | X | XVI | Mutalomycin | X |
| X | Narasin | X | | | |

While the present invention has been described with reference to particular embodiments thereof, it will be understood that numerous modifications may be made by those skilled in the art without actually departing from the spirit and scope of the invention.

What is claimed is:

1. A process for promoting growth and enhancing feed efficiency of food-producing mammals, which process comprises administering to food-producing mammals an animal feed composition containing a growth-promoting and feed efficiency-enhancing amount of a biomass containing a zinc antibiotic complex, to promote growth and enhance feed efficiency of the mammals, said biomass being prepared by:

(a) fermenting a broth inoculated with a Streptomyces microorganism capable of producing lysocellin by fermentation of the broth for a period of time and under suitable fermentation conditions in order to produce lysocellin in said fermentation broth;

(b) providing in the lysocellin-containing fermentation broth a water-soluble zinc salt in an amount sufficient to form a zinc complex of lysocellin, which complex is insoluble in the fermentation broth; and (c) recovering said biomass of insoluble material from said fermentation broth, said biomass containing both a zinc complex of lysocellin and insoluble zinc complexes of residual nitrogen-containing compounds present in the fermentation broth.

2. A process in accordance with claim 1 wherein, in preparing the zinc lysocellin complex-containing biomass, the fermentation of the inoculated broth is conducted at a temperature of from about 25° C. to about 35° C. and at a pH of from about 6.5 to 7.5.

3. A process in accordance with claim 2 wherein, in preparing the zinc lysocellin complex-containing biomass, the zinc salt added to the fermentation broth is selected from the group consisting of zinc chloride and zinc sulfate.

4. A process in accordance with claim 3 wherein, in preparing the zinc lysocellin complex-containing biomass, the pH of the fermentation broth is adjusted to within the range of from about 6.5 to 7.5 after the zinc salt is provided in said fermentation broth.

5. A process in accordance with claim 2 wherein, in preparing the zinc lysocellin complex-containing biomass, the water-soluble zinc salt is added to the fermentation broth in an amount sufficient to provide a zinc content of from about 3 to 12 weight percent on a dry basis in said biomass.

6. A process in accordance with claim 5 wherein the food-producing mammals are ruminants and the feed composition is administered in amounts sufficient to provide from about 1 to 200 milligrams of the zinc complex per head per day.

7. A process in accordance with claim 3 wherein, in preparing the zinc lysocellin complex-containing biomass, the water-soluble zinc salt is added to the fermentation broth in an amount sufficient to provide a zinc content of from about 3 to 12 weight percent on a dry basis in said biomass.

8. A process in accordance with claim 7 wherein the food-producing mammals are ruminants and the feed composition is administered in amounts sufficient to provide from about 1 to 200 milligrams of the zinc complex per head per day.

9. A process in accordance with claim 4 wherein, in preparing the zinc lysocellin complex-containing biomass, the water-soluble zinc salt is added to the fermentation broth in the amount sufficient to provide a zinc content of from about 3 to 12 weight percent on a dry basis in said biomass.

10. A process in accordance with claim 9 wherein the food-producing mammals are ruminants and the feed composition is administered in amounts sufficient to provide from about 1 to 200 milligrams of the zinc complex per head per day.

11. A process for promoting growth and enhancing feed efficiency of food-producing mammals, which process comprises administering to food-producing mammals an animal feed composition containing a growth-promoting and feed efficiency-enhancing amount of a biomass containing a zinc complex of lysocellin, to promote growth and enhance feed efficiency of the mammals, said biomass being prepared by:

(a) fermenting a broth inoculated with a microorganism capable of producing lysocellin by fermentation of the broth for a period of time and under suitable fermentation conditions in order to produce lysocellin in said fermentation broth;

(b) providing in the lysocellin-containing fermentation broth a water-soluble zinc salt in an amount sufficient to form a zinc complex of lysocellin, which complex is insoluble in the fermentation broth and is a part of a biomass formed in said broth during fermentation; and (c) recovering said biomass of insoluble material from said fermentation broth.

* * * * *

UNITED STATES PATENT AND TRADEMARK OFFICE
CERTIFICATE OF CORRECTION

PATENT NO. : 4,933,364

DATED : Jun. 12, 1990

INVENTOR(S) : Ivy et al.

It is certified that error appears in the above-identified patent and that said Letters Patent is hereby corrected as shown below:

Col. 15, line 67, "Ukrthern Utilization Laboratory" should be --Northern Utilization Laboratory--.

Signed and Sealed this

Twenty-seventh Day of April, 1993

Attest:

MICHAEL K. KIRK

Attesting Officer    Acting Commissioner of Patents and Trademarks